US011174230B2

(12) United States Patent
Kamal et al.

(10) Patent No.: US 11,174,230 B2
(45) Date of Patent: Nov. 16, 2021

(54) (E)-4-(4-ACRYLAMIDOPHENOXY)-N-METHYLPICOLINAMIDE CONJUGATES AS POTENTIAL ANTICANCER AGENTS

(71) Applicant: Council of Scientific & Industrial Research, New Delhi (IN)

(72) Inventors: Ahmed Kamal, Hyderabad (IN); Velma Ganga Reddy, Hyderabad (IN); Riyaz Syed, Hyderabad (IN); Suresh Babu Korrapati, Hyderabad (IN); Poornachandra Yedla, Hyderabad (IN); Ganesh Kumar Chityal, Hyderabad (IN)

(73) Assignee: Council of Scientific & Industrial Research, New Delhi (IN)

( * ) Notice: Subject to any disclaimer, the term of this patent is extended or adjusted under 35 U.S.C. 154(b) by 679 days.

(21) Appl. No.: 16/071,105

(22) PCT Filed: Jan. 4, 2017

(86) PCT No.: PCT/IN2017/050004
§ 371 (c)(1),
(2) Date: Jul. 19, 2018

(87) PCT Pub. No.: WO2017/125946
PCT Pub. Date: Jul. 27, 2017

(65) Prior Publication Data
US 2021/0163413 A1    Jun. 3, 2021

(30) Foreign Application Priority Data
Jan. 20, 2016 (IN) .............................. 201611002015

(51) Int. Cl.
| | | |
|---|---|---|
| C07D 213/81 | (2006.01) | |
| A61P 35/00 | (2006.01) | |
| C07D 401/12 | (2006.01) | |
| C07D 405/12 | (2006.01) | |
| C07D 409/12 | (2006.01) | |

(52) U.S. Cl.
CPC ............ *C07D 213/81* (2013.01); *A61P 35/00* (2018.01); *C07D 401/12* (2013.01); *C07D 405/12* (2013.01); *C07D 409/12* (2013.01)

(58) Field of Classification Search
CPC .. C07D 213/81; C07D 405/12; C07D 409/12; C07D 401/12; A61P 35/00
See application file for complete search history.

(56) References Cited

FOREIGN PATENT DOCUMENTS

EP    2942345 A1    11/2015

OTHER PUBLICATIONS

IUPAC Compendium of Chemical Terminology—Antibiotic—(2014) p. 1.*
Wilhelm et al., "Bay 43-9006 Exhibits Broad Spectrum Oral Antitumor activity and Targets the RAF/MEK/ERK Pathway and Receptor Tyrosine Kinases Involved in Tumor Progression and Angiogenesis", Cancer Research, American Association for Cancer Research, US, vol. 64, No. 19, 2004, pp. 7099-7109.
Leslie et al., "Phenylcinnamides as Novel Antimitotic Agents", Journal of Medicinal Chemistry, vol. 53, No. 10, 2010, pp. 3964-3972.
Niculescu_Duvaz et al., "Novel Inhibitors of B-RAF Based on a Pyrazine Scaffold. Generation of a Nanomolar Lead", Journal of Medicinal Chemistry, American Chemical Society, US, vol. 49, No. 1, 2006, pp. 407-416.
Anchoori et al., "Novel Microtubule-Interacting Phenoxy Pyridine and Phenyl Sulfanyl Pyridine Analogues for Cancer Therapy", Journal of Medical Chemistry, 2008, vol. 51, No. 19, pp. 5953-5957; NIH Public Access Author Manuscript.
Asakawa et al., "[11C]Sorafenib; Radiosynthesis and preliminary PET study of brain uptake in P-gp/Bcrp knockout mice", Bioorganic & Medicinal Chemistry Letters, vol. 21, 2011, pp. 2220-2223.
Chang et al., "Sorafenib (BAY 43-9006) inhibits tumor growth and vascularization and induces tumor apoptosis and hypoxia in RCC xenograft models", Cancer Chemother Pharmacol., vol. 59, 2007, pp. 561-574.
Wellbrock et al., "The RAF Proteins Take Centre Stage", Molecular Cell Biology, vol. 5, 2004, pp. 875-885.
Tuveson et al., "BRAF as a potential therapeutic target in melanoma and other malignancies", Cancer Cell, vol. 4, 2003, pp. 95-98.
International Search Report and Written Opinion, pertaining to PCT/IN2017/050004 dated Mar. 29, 2017.

* cited by examiner

*Primary Examiner* — John M Mauro
(74) *Attorney, Agent, or Firm* — Dinsmore & Shohl, LLP

(57) ABSTRACT

The present invention relates to a compound of formula A useful as potential anticancer agents against human cancer cell lines and process for the preparation thereof.

Formula A

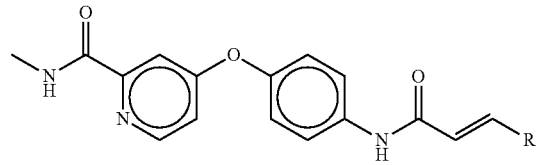

6 Claims, 1 Drawing Sheet

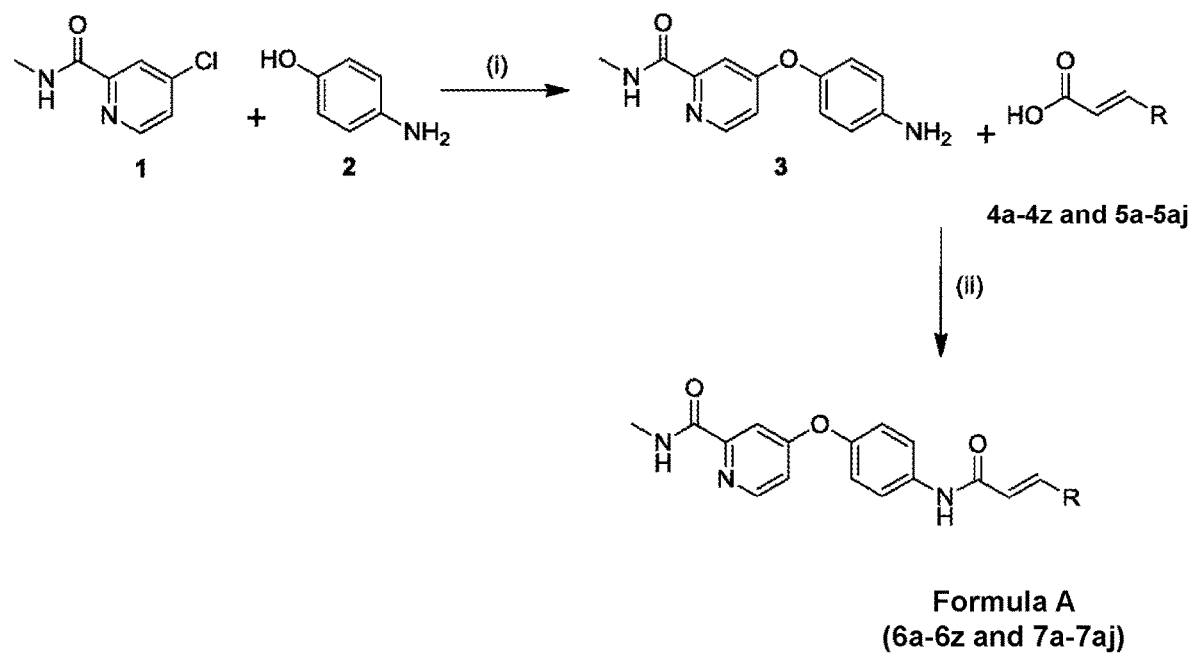

(E)-4-(4-ACRYLAMIDOPHENOXY)-N-METHYLPICOLINAMIDE CONJUGATES AS POTENTIAL ANTICANCER AGENTS

FIELD OF THE INVENTION

The present invention relates to (E)-4-(4-acrylamidophenoxy)-N-methylpicolinamide conjugates of formula A.

Formula A

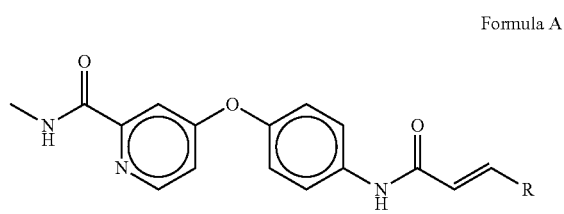

wherein R is selected from

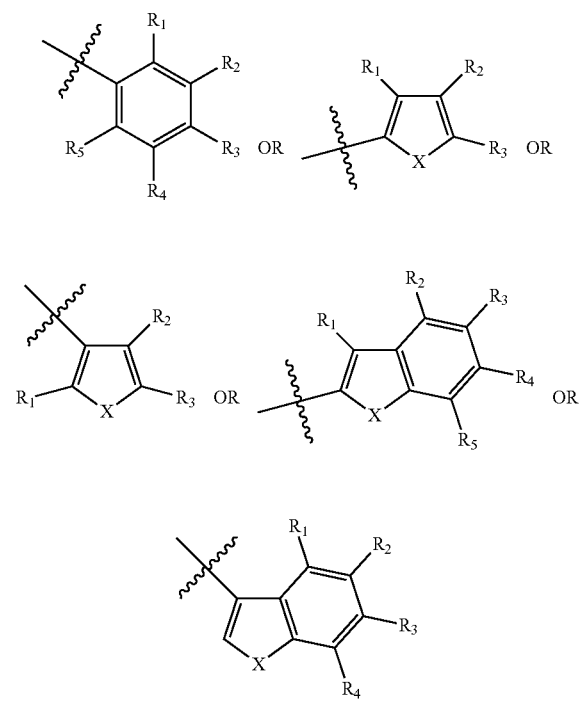

$R_1$ to $R_5$ is independently selected from the group consisting of H, Cl, F, Br, $CH_3$, $C_2H_5$, $CH(CH_3)_2$, $OCH_3$, $CF_3$, $OCF_3$, OH, $NO_2$ or CN;

X is selected from O, N or S.

Particularly, present invention relates to the synthesis and biological evaluation of (E)-4-(4-acrylamidophenoxy)-N-methylpicolinamide conjugates of formula A as potential anticancer agents.

BACKGROUND OF THE INVENTION

Protein tyrosine kinases are presently familiar as significant molecular targets for drug development in the treatment of several disorders, predominantly in the treatment of proliferative disorders. Dysregulation of tyrosine kinase activity has emerged as a major mechanism by which cancer cells avoid normal physiological constraints on growth, proliferation and survival.

Raf proteins are subject to complex regulation, which is reflected by the presence of numerous phosphorylation sites that are distributed throughout the proteins. Some of the sites are conserved in all three isoforms, which indicates common mechanisms of regulation, but others are not conserved, which shows that these proteins can be independently regulated. There are three Raf isoforms in mammals, A-Raf, B-Raf and C-Raf, all of which can act as downstream effectors of RAS. Although they show considerable sequence similarities, they also exhibit distinct roles in development, in addition to significant biochemical and functional differences. Raf proteins are subject to complex regulation, which is reflected by the presence of numerous phosphorylation sites that are distributed throughout the proteins. In particular, the high basal kinase activity of B-Raf may explain why mutated forms of only this isoform have been found in human cancers. B-Raf is part of a conserved signal transduction pathway that regulates cellular responses to extra cellular signals (Wellbrock et al, *Mol. Cell. Boil.*, 2004, 5, 875-885). B-Raf is mutated in around 7% of human cancers, extensively such as melanoma, ovarian and thyroid cancers (Davies et al, *Cancer Cell.*, 2003, 2, 95-98), in this the most common mutation is a glutamic acid for valine substitution at position 600 (V600E) (Niculescu-Duvas er cr/., *J. Med. Chem.*, 2006, 49, 407-416).

Sorafenib is a small-molecule multi-kinase inhibitor that inhibits kinases such as Raf kinase, vascular endothelial growth factor receptor (VEGFR), and platelet-derived growth factor receptor (PDGFR)-β tyrosine kinases (Wilhelm et al, *Cancer Res.*, 2004, 64(19):7099-109). This kinase inhibitor having flat, aromatic molecules which mimic the adenine group of ATP which binds to a highly conserved ATP-binding pocket to inhibit kinase function. It is a bi-aryl urea which inhibits cell surface tyrosine kinase receptors (e.g. vascular endothelial growth factor receptors and platelet-derived growth factor receptor-beta) and downstream intracellular serine/threonine kinases (e.g. Raf-1, wild-type B-Raf and mutant B-Raf); these kinases are involved in inhibition of tumor-cell proliferation, angiogenesis and increases the rate of apoptosis in a wide range of tumor models (Chang and coworkers, *Cancer Chemother Pharmacol.*, 2007; 59(5): 561-74). However, the structural features of sorafenib demonstrated multi-kinase inhibitory activities with potent anti-antigenic properties via the inhibition of pro-angiogenic receptor tyrosine kinases (RTKs), such as the VEGFR. As a result, sorafenib displays multi-inhibitory action in the RAF/MEK/ERK pathway and RTKs to combat tumour angiogenesis. This drug has shown marked clinical efficiency and safety in advanced renal cell and hepatocellular carcinoma, it has been approved for the treatment of these cancers in patients (Asakawa and coworkers, *Bioorg. Med. Chem. Lett.*, 2011, 21, 2220-2223). The present work involves the synthesis of new molecules based on sorafenib ring system. One of the major issues of selectivity in the development of anticancer agents has been addressed by these molecules as they are highly selective towards some specific cancer cell lines. In continuation of these efforts and the interest in this laboratory structural modifications of the sorafenib, an efficient access to the construction of some new (E)-4-(4-acrylamidophenoxy)-N-methylpicolinamide conjugates (6a-z to 7a-aj) with improved cytotoxic activity in certain cell lines is described.

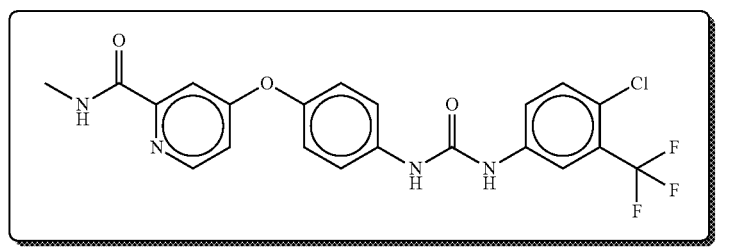

Sorafenib

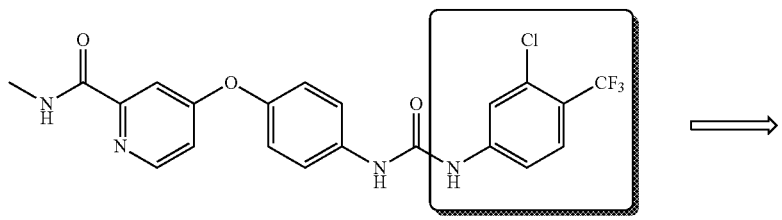

Sorafenib

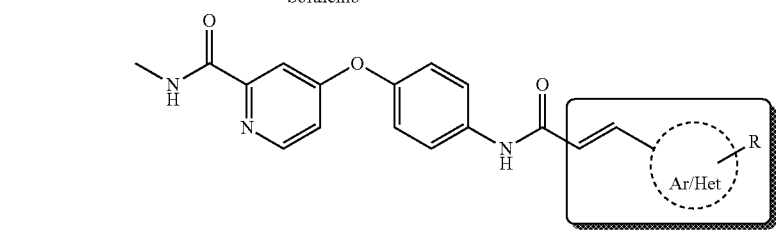

New conjugates (6a-z to 7a-aj)

OBJECTIVE OF THE INVENTION

The main objective of the present invention is to provide (E)-4-(4-acrylamidophenoxy)-N-methylpicolinamide conjugates of formula A as potential antitumor agents.

Another object of the present invention is to provide a process for the preparation of (E)-4-(4-acrylamidophenoxy)-N-methylpicolinamide conjugates of formula A.

BRIEF DESCRIPTION OF THE DRAWING

The FIGURE represents process steps for the preparation of compound of formula A wherein reagents and conditions are as follows: (i) KOt-Bu, K₂CO₃, DMF, 80° C., 4 h; (ii) EDCI, HOBT, DMF, 0° C.-room temperature (20 to 30° C.), 12 h.

SUMMARY OF THE INVENTION

Accordingly, present invention provides compound of formula A

Formula A

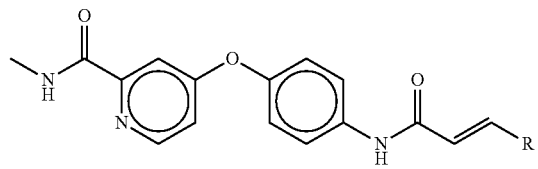

wherein R is selected from

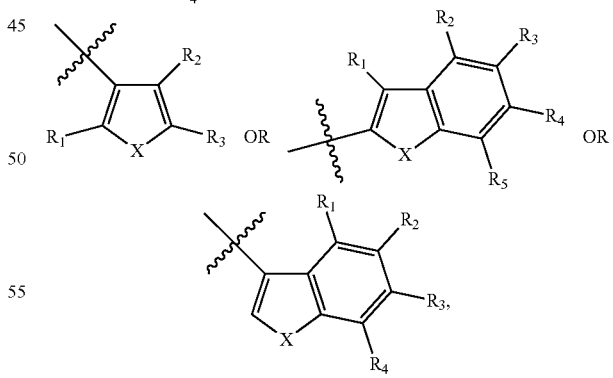

$R_1$, $R_2$, $R_3$, $R_4$ and $R_5$ is independently selected from the group consisting of H, Cl, F, Br, CH₃, C₂H₅, CH(CH₃)₂, OCH₃, CF₃, OCF₃, OH, NO₂ or CN;

X is selected from O, N or S.

In an embodiment of the present invention, (E)-4-(4-acrylamidophenoxy)-N-methylpicolinamide conjugates of formula A represented by the compounds of general formulae 6a-z to 7a-aj which are as follow:

(E)-4-(4-(3-(2-methoxyphenyl)acrylamido)phenoxy)-N-methylpicolinamide (6a);
(E)-4-(4-(3-(4-methoxyphenyl)acrylamido)phenoxy)-N-methylpicolinamide (6b);
(E)-4-(4-(3-(2,3-dimethoxyphenyl)acrylamido)phenoxy)-N-methylpicolinamide (6c);
(E)-N-methyl-4-(4-(3-(3,4,5-trimethoxyphenyl)acrylamido)phenoxy)picolinamide (6d);
(E)-4-(4-(3-(2,5-dimethoxyphenyl)acrylamido)phenoxy)-N-methylpicolinamide (6e);
(E)-4-(4-(3-(3,4-dimethoxyphenyl)acrylamido)phenoxy)-N-methylpicolinamide (6f);
(E)-4-(4-(3-(3-hydroxyphenyl)acrylamido)phenoxy)-N-methylpicolinamide (6g);
(E)-4-(4-(3-(4-hydroxyphenyl)acrylamido)phenoxy)-N-methylpicolinamide (6h);
(E)-4-(4-(3-(3-hydroxy-4-methoxyphenyl)acrylamido)phenoxy)-N-methylpicolinamide (6i);
(E)-4-(4-(3-(2-chlorophenyl)acrylamido)phenoxy)-N-methylpicolinamide (6j);
(E)-4-(4-(3-(3-chlorophenyl)acrylamido)phenoxy)-N-methylpicolinamide (6k);
(E)-4-(4-(3-(4-chlorophenyl)acrylamido)phenoxy)-N-methylpicolinamide (6l);
(E)-4-(4-(3-(3,4-dichlorophenyl)acrylamido)phenoxy)-N-methylpicolinamide (6m);
(E)-4-(4-(3-(3-fluorophenyl)acrylamido)phenoxy)-N-methylpicolinamide (6n);
(E)-4-(4-(3-(4-fluorophenyl)acrylamido)phenoxy)-N-methylpicolinamide (6o);
(E)-4-(4-(3-(2,4-difluorophenyl)acrylamido)phenoxy)-N-methylpicolinamide (6p);
(E)-4-(4-(3-(3,4-difluorophenyl)acrylamido)phenoxy)-N-methylpicolinamide (6q);
(E)-N-methyl-4-(4-(3-(2-(trifluoromethyl)phenyl)acrylamido)phenoxy)picolinamide (6r);
(E)-N-methyl-4-(4-(3-(3-(trifluoromethyl)phenyl)acrylamido)phenoxy)picolinamide (6s);
(E)-N-methyl-4-(4-(3-(4-(trifluoromethyl)phenyl)acrylamido)phenoxy)picolinamide (6t);
(E)-N-methyl-4-(4-(3-(2-(trifluoromethoxy)phenyl)acrylamido)phenoxy)picolinamide (6u);
(E)-N-methyl-4-(4-(3-(3-(trifluoromethoxy)phenyl)acrylamido)phenoxy)picolinamide (6v);
(E)-N-methyl-4-(4-(3-(4-(trifluoromethoxy)phenyl)acrylamido)phenoxy)picolinamide (6w);
(E)-4-(4-(3-(4-fluoro-3-(trifluoromethoxy)phenyl)acrylamido)phenoxy)-N-methylpicolinamide (6x);
(E)-4-(4-(3-(4-chloro-3-(trifluoromethoxy)phenyl)acrylamido)phenoxy)-N-methylpicolinamide (6y);
(E)-N-methyl-4-(4-(3-(4-nitrophenyl)acrylamido)phenoxy)picolinamide (6z);
(E)-4-(4-(3-(1H-pyrrol-3-yl)acrylamido)phenoxy)-N-methylpicolinamide (7a);
(E)-4-(4-(3-(furan-2-yl)acrylamido)phenoxy)-N-methylpicolinamide (7b);
(E)-N-methyl-4-(4-(3-(5-methylfuran-2-yl)acrylamido)phenoxy)picolinamide (7c);
(E)-4-(4-(3-(5-ethylfuran-2-yl)acrylamido)phenoxy)-N-methylpicolinamide (7d);
(E)-4-(4-(3-(3-bromofuran-2-yl)acrylamido)phenoxy)-N-methylpicolinamide (7e);
(E)-N-methyl-4-(4-(3-(5-nitrofuran-2-yl)acrylamido)phenoxy)picolinamide (7f);
(E)-N-methyl-4-(4-(3-(thiophen-2-yl)acrylamido)phenoxy)picolinamide (7g);
(E)-4-(4-(3-(4-bromothiophen-2-yl)acrylamido)phenoxy)-N-methylpicolinamide (7h);
(E)-N-methyl-4-(4-(3-(3-methylthiophen-2-yl)acrylamido)phenoxy)picolinamide (7i);
(E)-4-(4-(3-(5-cyanothiophen-2-yl)acrylamido)phenoxy)-N-methylpicolinamide (7j);
(E)-N-methyl-4-(4-(3-(4-methylthiophen-2-yl)acrylamido)phenoxy)picolinamide (7k);
(E)-N-methyl-4-(4-(3-(5-methylthiophen-2-yl)acrylamido)phenoxy)picolinamide (7l);
(E)-4-(4-(3-(benzofuran-2-yl)acrylamido)phenoxy)-N-methylpicolinamide (7m);
(E)-4-(4-(3-(7-methoxybenzofuran-2-yl)acrylamido)phenoxy)-N-methylpicolinamide (7n);
(E)-4-(4-(3-(benzo[b]thiophen-2-yl)acrylamido)phenoxy)-N-methylpicolinamide (7o);
(E)-4-(4-(3-(3-bromobenzo[b]thiophen-2-yl)acrylamido)phenoxy)-N-methylpicolinamide (7p);
(E)-N-methyl-4-(4-(3-(3-methylbenzo[b]thiophen-2-yl)acrylamido)phenoxy)picolinamide (7q);
(E)-4-(4-(3-(3-chlorobenzo[b]thiophen-2-yl)acrylamido)phenoxy)-N-methylpicolinamide (7r);
(E)-N-methyl-4-(4-(3-(5-methylbenzo[b]thiophen-2-yl)acrylamido)phenoxy)picolinamide (7s);
(E)-N-methyl-4-(4-(3-(4-methylbenzo[b]thiophen-2-yl)acrylamido)phenoxy)picolinamide (7t);
(E)-4-(4-(3-(1H-indol-3-yl)acrylamido)phenoxy)-N-methylpicolinamide (7u);
(E)-N-methyl-4-(4-(3-(7-methyl-1H-indol-3-yl)acrylamido)phenoxy)picolinamide (7v);
(E)-4-(4-(3-(7-ethyl-1H-indol-3-yl)acrylamido)phenoxy)-N-methylpicolinamide (7w);
(E)-4-(4-(3-(6-isopropyl-1H-indol-3-yl)acrylamido)phenoxy)-N-methylpicolinamide (7x);
(E)-4-(4-(3-(5-chloro-1H-indol-3-yl)acrylamido)phenoxy)-N-methylpicolinamide (7y);
(E)-4-(4-(3-(6-chloro-1H-indol-3-yl)acrylamido)phenoxy)-N-methylpicolinamide (7z);
(E)-4-(4-(3-(5-fluoro-1H-indol-3-yl)acrylamido)phenoxy)-N-methylpicolinamide (7aa);
(E)-4-(4-(3-(6-fluoro-1H-indol-3-yl)acrylamido)phenoxy)-N-methylpicolinamide (7ab);
(E)-4-(4-(3-(5-bromo-1H-indol-3-yl)acrylamido)phenoxy)-N-methylpicolinamide (7ac);
(E)-4-(4-(3-(6-bromo-1H-indol-3-yl)acrylamido)phenoxy)-N-methylpicolinamide (7ad);
(E)-4-(4-(3-(5-cyano-1H-indol-3-yl)acrylamido)phenoxy)-N-methylpicolinamide (7ae);
(E)-4-(4-(3-(6-cyano-1H-indol-3-yl)acrylamido)phenoxy)-N-methylpicolinamide (7af);
(E)-N-methyl-4-(4-(3-(5-methyl-1H-indol-3-yl)acrylamido)phenoxy)picolinamide (7ag);
(E)-N-methyl-4-(4-(3-(6-methyl-1H-indol-3-yl)acrylamido)phenoxy)picolinamide (7ah);
(E)-N-methyl-4-(4-(3-(5-nitro-1H-indol-3-yl)acrylamido)phenoxy)picolinamide (7ai);
(E)-N-methyl-4-(4-(3-(6-nitro-1H-indol-3-yl)acrylamido)phenoxy)picolinamide (7aj).

In another embodiment of the present invention, structural formulae of the representative compounds of formula A are:

-continued

6o

6p

6q

6r

6s

6t

6u

-continued

6v

6w

6x

6y

6z

7a

7b

7c
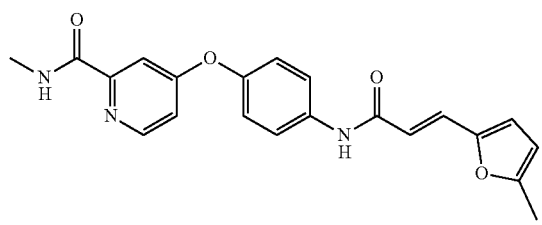
7d
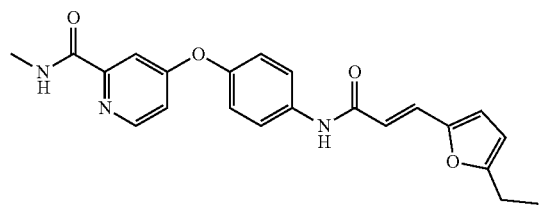
7e
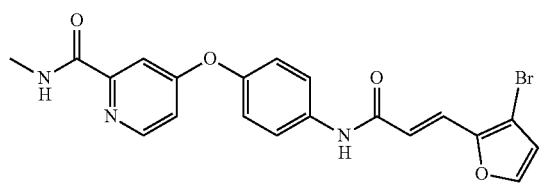
7f
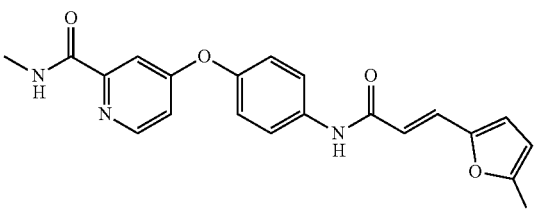
7g
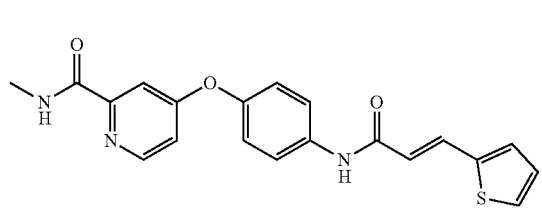
7h
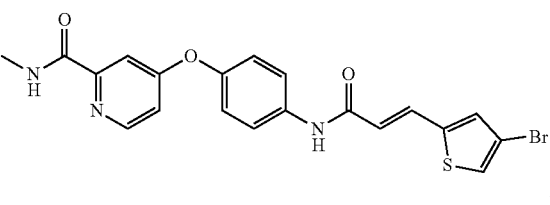
7i
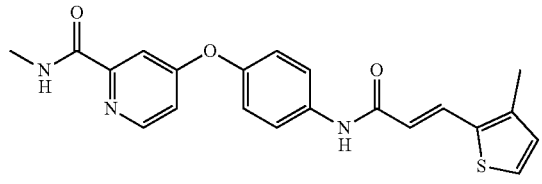
7j
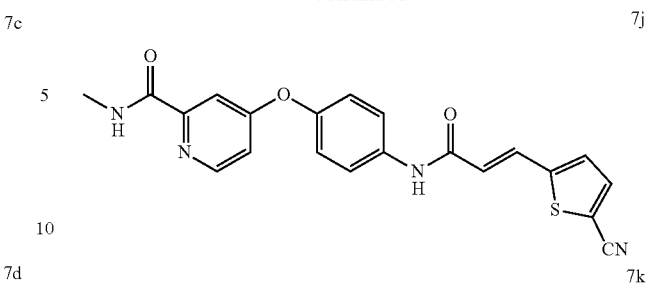
7k
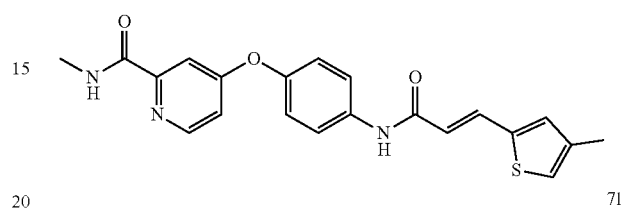
7l
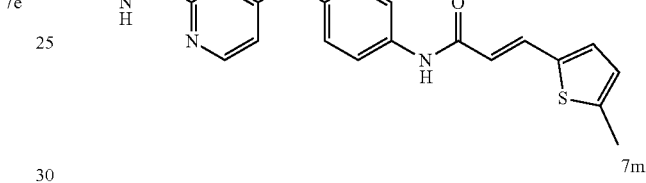
7m
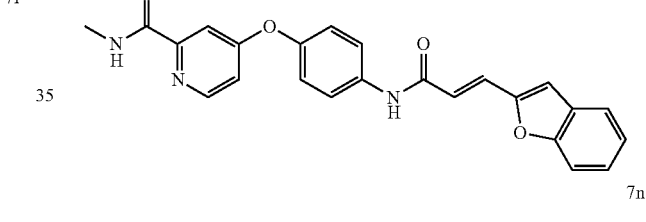
7n
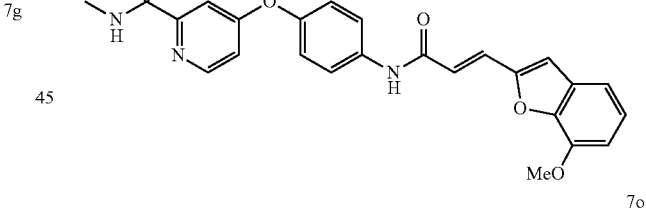
7o
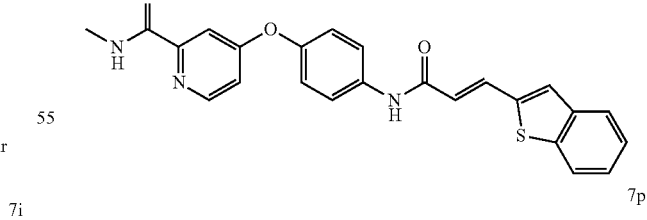
7p
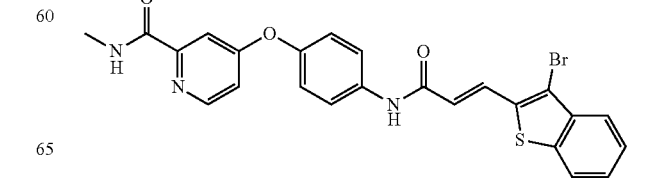

7q 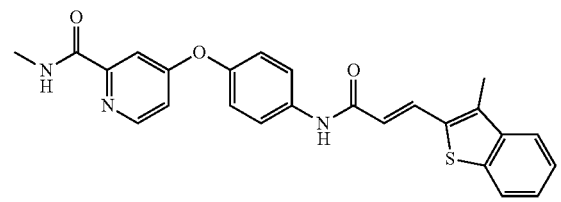
7r 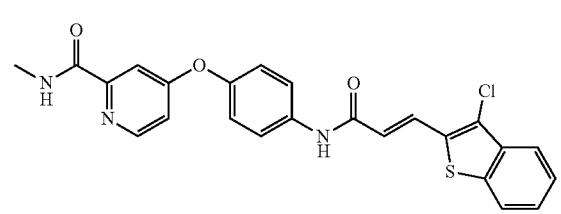
7s 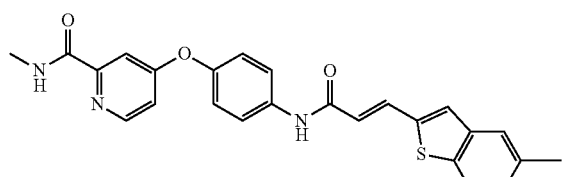
7t 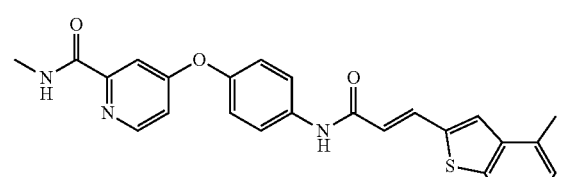
7u 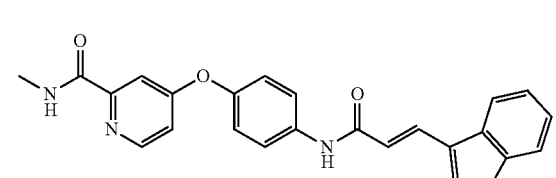
7v 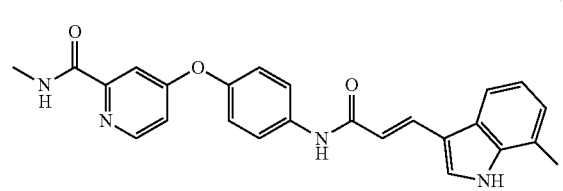
7w 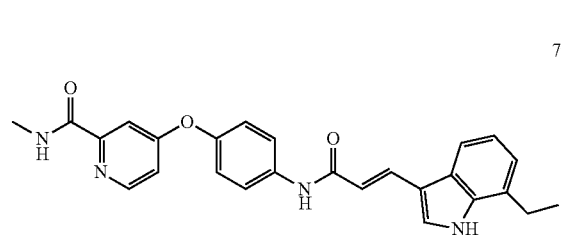
7x 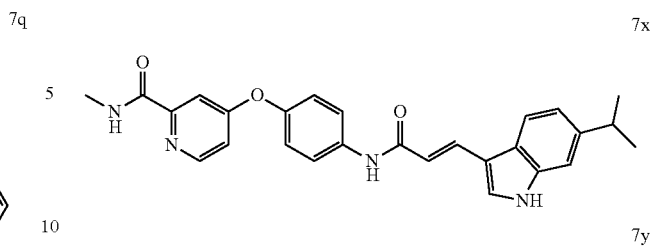
7y 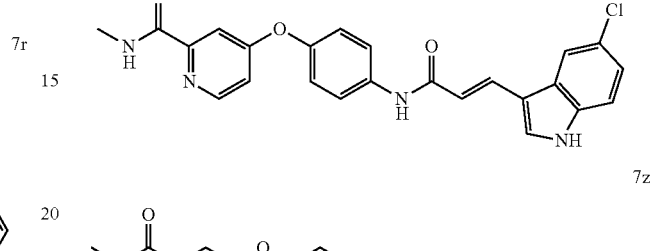
7z 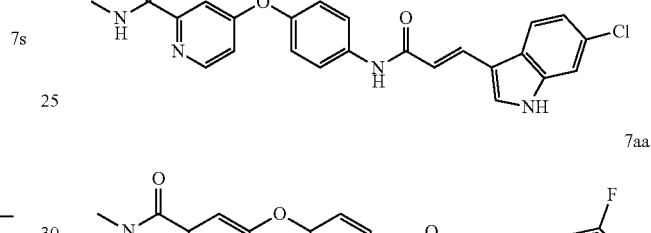
7aa 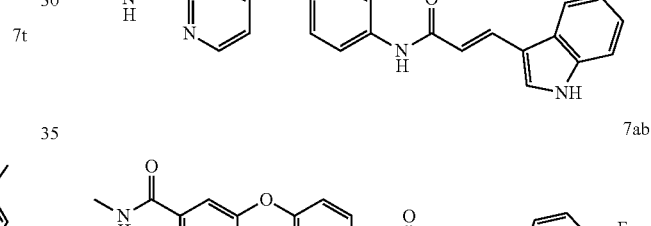
7ab 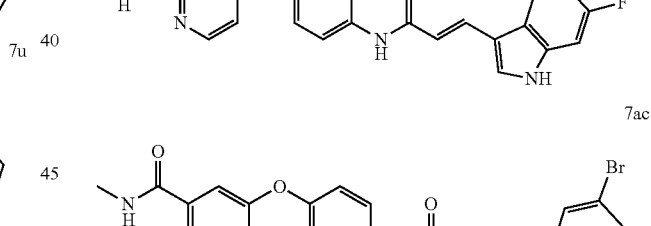
7ac 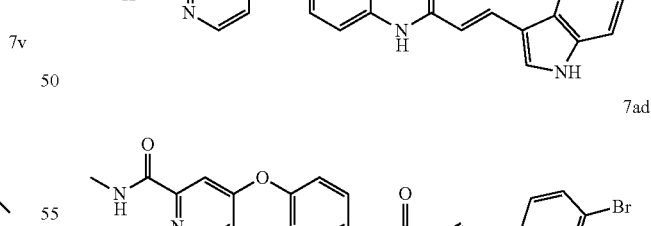
7ad 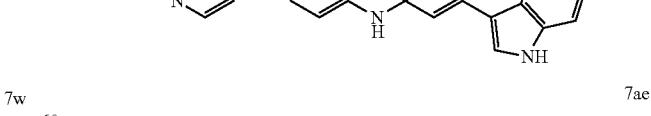
7ae 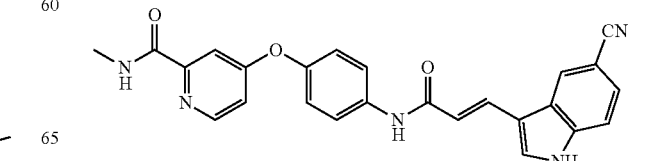

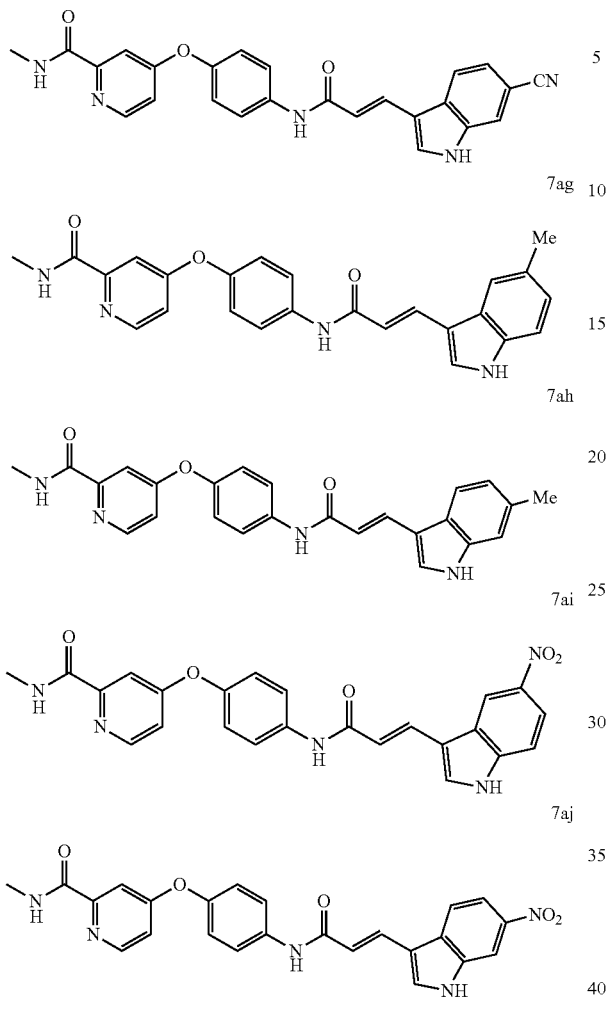

In yet another embodiment of the present invention, said compound exhibit significant anticancer activity as antitumour antibiotics against cancer cell lines selected from the group consisting of non-small cell lung cancer, colon cancer, prostate cancer, ovarian cancer and liver cancer.

In yet another embodiment of the present invention, $IC_{50}$ value of in vitro anti-cancer activity of formula A is in the range of 8 to 13 μM.

In yet another embodiment, present invention provides a process for the preparation of compounds of formula A comprising the steps of:

i) mixing the acid compound of formula 4a-z and 5a-aj with EDCI (1-Ethyl-3-(3-dimethylaminopropyl)carbodiimide) HOBT (Hydroxybenzotriazole), in dry DMF (Dimethylformamide) under nitrogen atmosphere with stirring at 0° C. for 15 to 20 min;

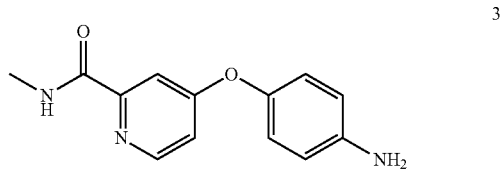

wherein R is selected from

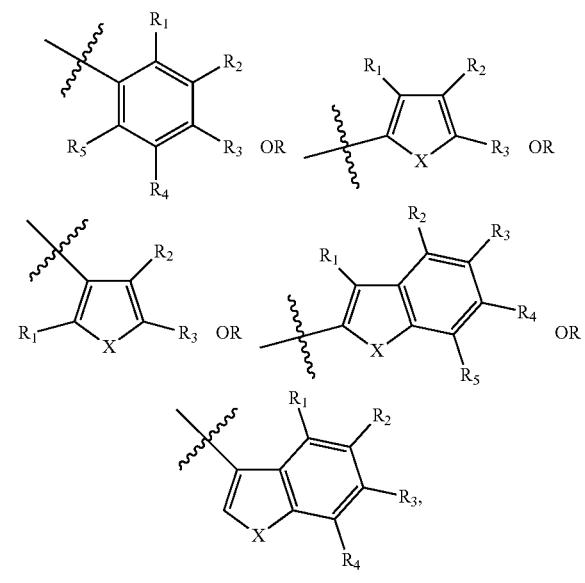

$R_1$ to $R_5$ is independently selected from the group consisting of H, Cl, F, Br, $CH_3$, $C_2H_5$, $CH(CH_3)_2$, $OCH_3$, $CF_3$, $OCF_3$, OH, $NO_2$ or CN;

X is selected from O, N or S.

ii) adding 4-(4-aminophenoxy)-N-methylpicolinamide of formula 3 in the mixture as obtained in step (i) with stirring at room temperature in the range of 20 to 30° C. for 10 to 12 h;

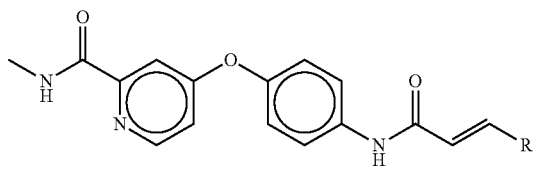

iii) cooling the mixture as obtained in step (ii), extracting, washing, drying, filtering and purifying by column chromatography to obtain compound of formula A.

In yet another embodiment, the solvent is DMF and DCM.

In yet another embodiment, the present invention provided the use of compound of formula A as anti-cancer agents

DETAILED DESCRIPTION OF THE INVENTION

Present invention provides compound of formula A

Formula A wherein R is selected from

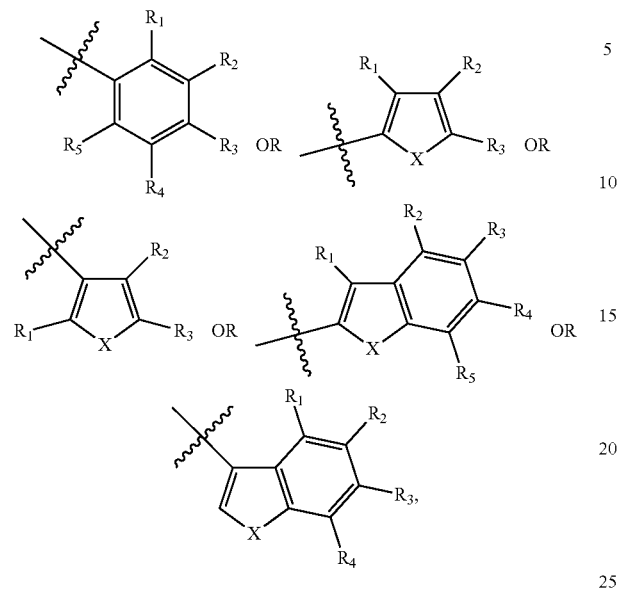

R$_1$ to R$_5$ is selected from the group consisting of H, Cl, F, Br, CH$_3$, C$_2$H$_5$, CH(CH$_3$)$_2$, OCH$_3$, CF$_3$, OCF$_3$, OH, NO$_2$ or CN; X is selected from O, N or S.

New (E)-4-(4-acrylamidophenoxy)-N-methylpicolinamide conjugates prepared by the known chemical reactions and procedures, in that some of the starting materials are commercially available. The major precursor 4-(4-aminophenoxy)-Nmethylpicolinamide formula 3 was prepared by using literature method (Anchoori et al. J. Med. Chem., 2008, 51, 5953-5957). Aromatic and hetero cyclic substituted acrylic acids are commercially available in the market. (E)-4-(4-acrylamidophenoxy)-N-methylpicolinamide conjugates of formula 6a-z and 7a-aj were synthesized as illustrated in the FIGURE.

To a solution of aromatic and hetero cyclic substituted acrylic acids (4a-z and 5a-aj, mmol) in dry dimethylformamide, EDCI (1-Ethyl-3-(3-dimethylaminopropyl)carbodiimide) (1.2 mmol) and HOBT (Hydroxybenzotriazole) (1.2 mmol) were added at 0° C. and the reaction mixture was stirred for 20 min. To the reaction mixture 4-(4-aminophenoxy)-N-methylpicolinamide (3, 1 mmol) was added and stirred at room temperature (20 to 30° C.) for 12 h. The contents of the reaction mixture were poured into ice-cold water (25 mL), extracted with ethyl acetate (3×15.0) and the combined organic phase was washed with brine, dried over anhydrous sodium sulfate, filtered and concentrated in vacuo. The obtained residue was purified by column chromatography using ethyl acetate-hexane (50%) as eluent to furnish pure (E)-4-(4-acrylamidophenoxy)-N-methylpicolinamide conjugates of formula 6a-z and 7a-aj in good yields (75-80%).

Aromatic and hetero cyclic substituted acrylic acids compound of formula 4a-z and 5a-aj are as follow:

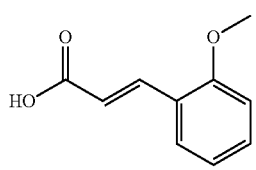
4a

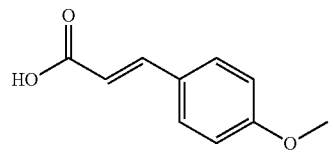
4b

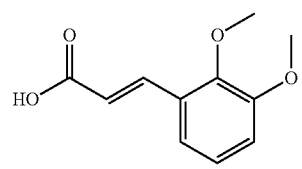
4c

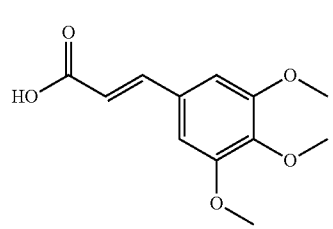
4d

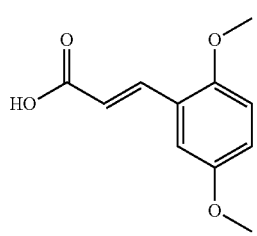
4e

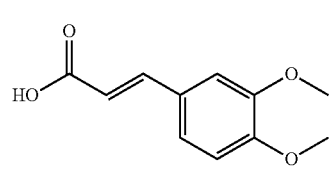
4f

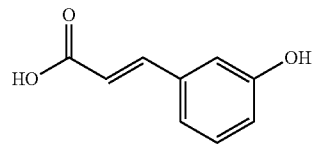
4g

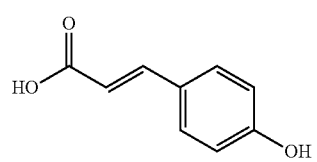
4h

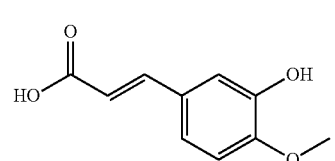
4i

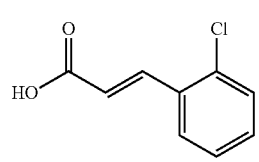
4j

-continued
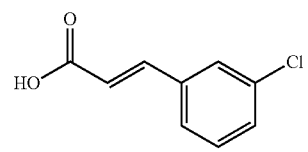
4k
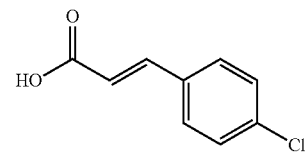
4l
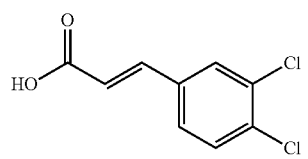
4m
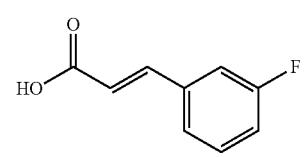
4n
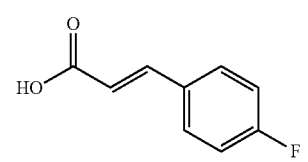
4o
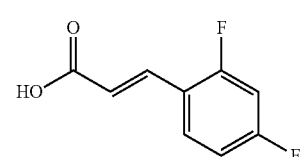
4p
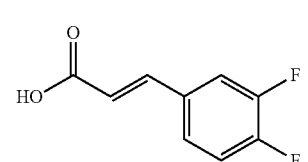
4q
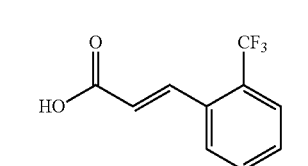
4r
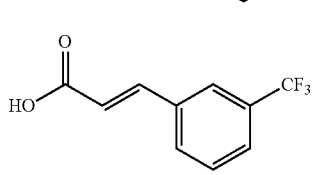
4s
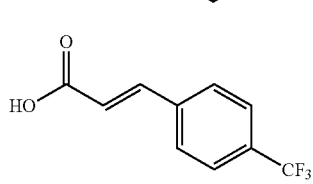
4t
-continued
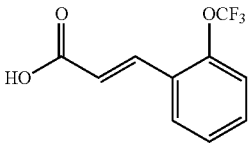
4u
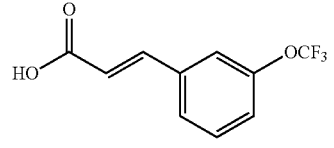
4v
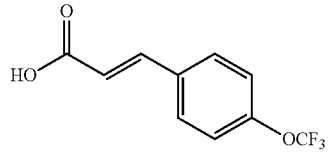
4w
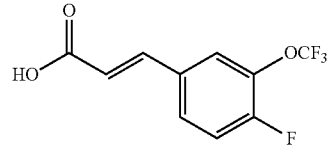
4x
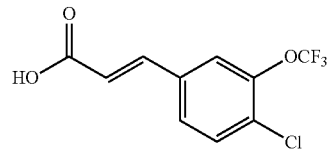
4y
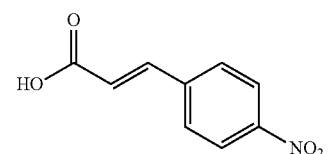
4z
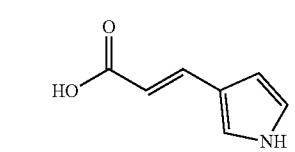
5a
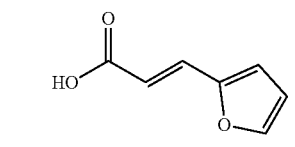
5b
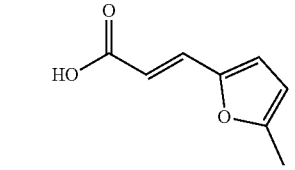
5c
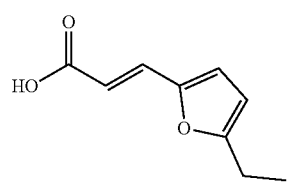
5d -continued
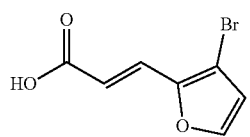
5e
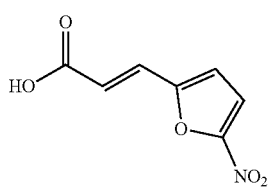
5f
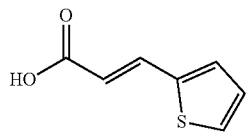
5g
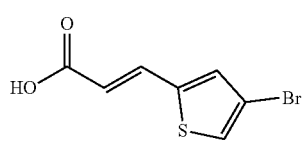
5h
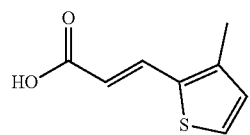
5i
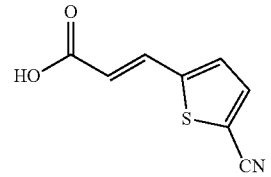
5j
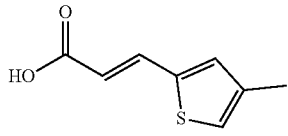
5k
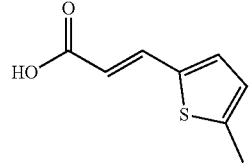
5l
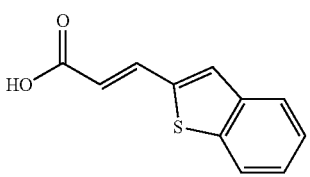
5m
-continued
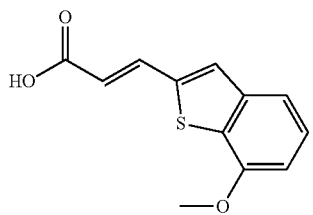
5n
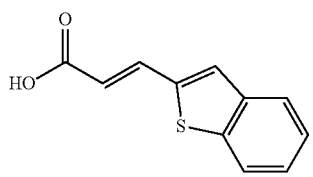
5o
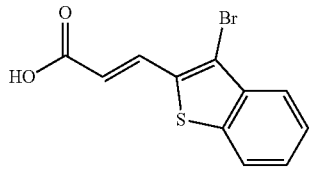
5p
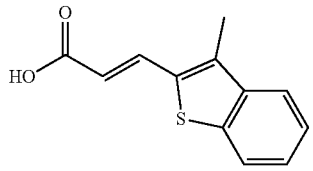
5q
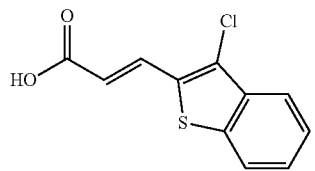
5r
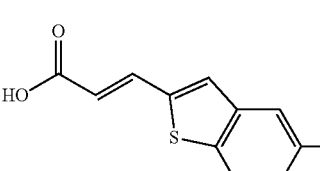
5s
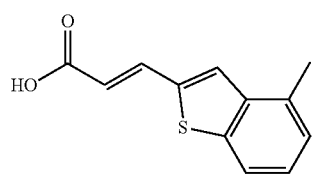
5t
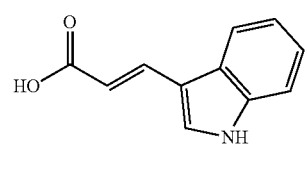
5u
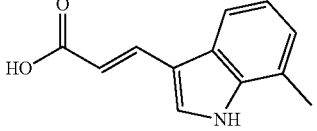
5v 5w 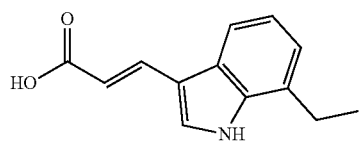

5x 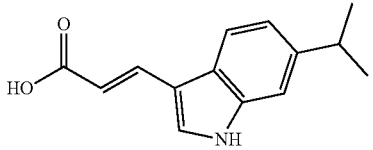

5y 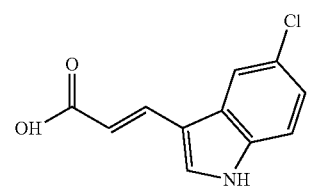

5z 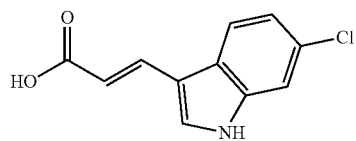

5aa 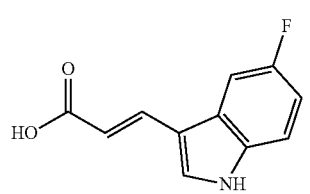

5ab 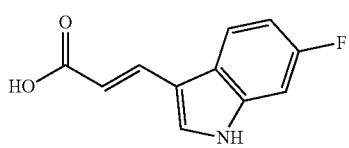

5ac 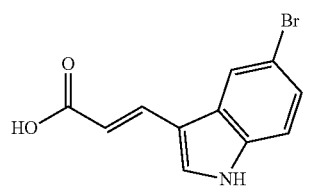

5ad 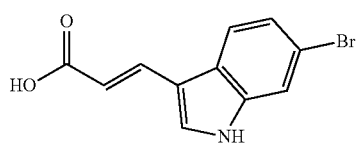

5ae 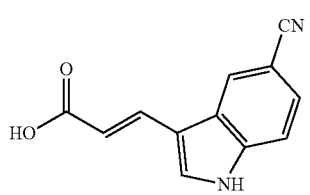

5af 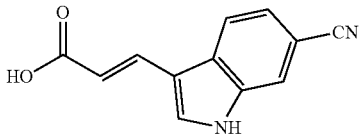

5ag 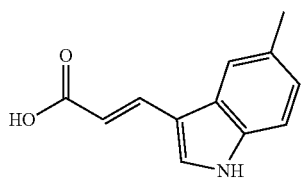

5ah 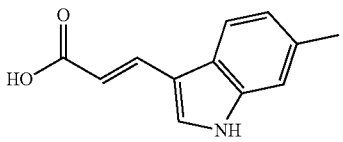

5ai 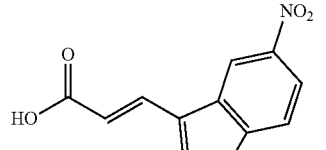

5aj 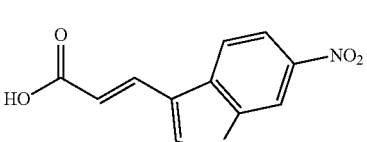

The synthesis of new congeners as illustrated in the FIGURE which comprise: The acid-amine coupling reaction between 4-(4-aminophenoxy)-N-methylpicolinamide formula 3 with aromatic acrylic acid compounds of formulae 4a-z and hetero cyclic acrylic acid compounds of formulae 5a-aj for the compounds (6a-6z to 7a-7aj), respectively. These newer (E)-4-(4-acrylamidophenoxy)-N-methylpicolinamide conjugates showed promising cytotoxic activity in various cancer cell lines.

EXAMPLES

The following examples are given by way of illustration and therefore should not be construed to limit the scope of the invention.

Example 1

(E)-4-(4-(3-(4-methoxyphenyl)acrylamido)phenoxy)-N-methylpicolinamide (6b)

To a solution of (E)-3-(4-methoxyphenyl)acrylic acid (89 mg, 0.5 mmol) in dry dimethylformamide, EDCI (115 mg, 0.6 mmol) and HOBT (81 mg, 0.6 mmol) were added at 0° C. and the reaction mixture was stirred for 20 min. To the reaction mixture 4-(4-aminophenoxy)-N-methylpicolinamide (121.5 mg, 0.5 mmol) was added and stirred at room temperature (25° C.) for 12 h. The contents of the reaction mixture were poured into ice-cold water (25 mL), extracted with ethyl acetate (3×15.0) and the combined organic phase was washed with brine, dried over anhydrous sodium sulfate, filtered and concentrated in vacuo. The obtained residue was purified by column chromatography using ethyl acetate-hexane (0-50%) as eluent to give 157 mg (78%) of analytically pure compound (6b). mp: 202-204° C.; $^1$H NMR (CDCl3): δ 9.77 (s, 1H), 8.39 (d, J=5.66 Hz, 1H), 8.19 (s, 1H), 7.82 (d, J=8.87 Hz, 2H), 7.65 (q, J=7.17, 9.63 Hz, 2H), 7.52 (d, J=8.49 Hz, 3H), 7.06 (d, J=8.87 Hz, 2H), 6.98-6.90 (m, 3H), 6.66 (d, J=15.67 Hz, 1H), 3.85 (s, 3H), 2.99 (d, J=4.91 Hz, 3H); MS (ESI): m/z 404 [M+H]$^+$.

Example 2

(E)-4-(4-(3-(2,3-dimethoxyphenyl)acrylamido)phenoxy)-N-methylpicolinamide (6c)

To a solution of (E)-3-(2,3-dimethoxyphenyl)acrylic acid (104.1 mg, 0.5 mmol) in dry dimethylformamide, EDCI (115 mg, 0.6 mmol) and HOBT (81 mg, 0.6 mmol) were added at 0° C. and the reaction mixture was stirred for 20 min. To the reaction mixture 4-(4-aminophenoxy)-N-methylpicolinamide (121.5 mg, 0.5 mmol) was added and stirred at room temperature (30° C.) for 12 h. The contents of the reaction mixture were poured into ice-cold water (25 mL), extracted with ethyl acetate (3×15.0) and the combined organic phase was washed with brine, dried over anhydrous sodium sulfate, filtered and concentrated in vacuo. The obtained residue was purified by column chromatography using ethyl acetate-hexane (0-50%) as eluent to give 160 mg (74%) of analytically pure compound (6c). mp: 128-131° C.; $^1$H NMR (CDCl3): δ 8.38 (s, 1H), 8.07-8.01 (m, 2H), 7.89 (s, 1H), 7.71 (s, 1H), 7.70 (d, J=2.594 Hz, 2H), 7.12 (d, J=7.78 Hz, 1H), 7.07-7.03 (m, 3H), 6.96 (dd, J=2.44, 5.49 Hz, 1H), 6.94 (d, J=7.17 Hz, 1H), 6.68 (d, J=15.71 Hz, 1H), 3.89 (s, 3H), 3.87 (s, 3H), 3.02 (d, J=5.03 Hz, 3H); MS (ESI): m/z 434 [M+H]$^+$.

Example 3

(E)-N-methyl-4-(4-(3-(3,4,5-trimethoxyphenyl)acrylamido)phenoxy)picolinamide (6d)

To a solution of (E)-3-(3,4,5-trimethoxyphenyl)acrylic acid (119 mg, 0.5 mmol) in dry dimethylformamide, EDCI (115 mg, 0.6 mmol) and HOBT (81 mg, 0.6 mmol) were added at 0° C. and the reaction mixture was stirred for 20 min. To the reaction mixture 4-(4-aminophenoxy)-N-methylpicolinamide (121.5 mg, 0.5 mmol) was added and stirred at room temperature (20° C.) for 12 h. The contents of the reaction mixture were poured into ice-cold water (25 mL), extracted with ethyl acetate (3×15.0) and the combined organic phase was washed with brine, dried over anhydrous sodium sulfate, filtered and concentrated in vacuo. The obtained residue was purified by column chromatography using ethyl acetate-hexane (0-50%) as eluent to give 182 mg (79%) of analytically pure compound (6d). mp: 148-150° C.; $^1$H NMR (CDCl3): δ 8.38 (s, 1H), 8.09-8.03 (m, 2H), 7.71-7.65 (m, 4H), 7.05 (d, J=8.92 Hz, 2H), 6.99 (dd, J=2.56, 5.62 Hz, 1H), 6.75 (s, 2H), 6.51 (d, J=15.52 Hz, 1H), 3.89 (s, 3H), 3.87 (s, 6H), 3.02 (d, J=5.13 Hz, 3H); MS (ESI): m/z 464 [M+H]$^+$.

Example 4

(E)-4-(4-(3-(2,5-dimethoxyphenyl)acrylamido)phenoxy)-N-methylpicolinamide (6e)

To a solution of (E)-3-(2,5-dimethoxyphenyl)acrylic acid (104.1 mg, 0.5 mmol) in dry dimethylformamide, EDCI (115 mg, 0.6 mmol) and HOBT (81 mg, 0.6 mmol) were added at 0° C. and the reaction mixture was stirred for 20 min. To the reaction mixture 4-(4-aminophenoxy)-N-methylpicolinamide (121.5 mg, 0.5 mmol) was added and stirred at room temperature (25° C.) for 12 h. The contents of the reaction mixture were poured into ice-cold water (25 mL), extracted with ethyl acetate (3×15.0) and the combined organic phase was washed with brine, dried over anhydrous sodium sulfate, filtered and concentrated in vacuo. The obtained residue was purified by column chromatography using ethyl acetate-hexane (0-50%) as eluent to give 153 mg (71%) of analytically pure compound (6e). mp: 133-135° C.; $^1$H NMR (CDCl3): δ 8.38 (d, J=5.62 Hz, 1H), 8.03 (d, J=3.66 Hz, 1H), 7.98 (d, J=15.65 Hz, 1H), 7.74 (s, 1H), 7.70 (d, J=2.32 Hz, 2H), 7.68 (s, 1H), 708-7.03 (m, 3H), 6.96 (dd, J=2.56, 5.50 Hz, 1H), 6.89 (d, J=2.93 Hz, 1H), 6.87 (d, J=8.92 Hz, 1H), 6.70 (d, J=15.65 Hz, 1H), 3.86 (s, 3H), 3.79 (s, 3H), 3.02 (d, J=5.13 Hz, 3H); MS (ESI): m/z 434 [M+H]$^+$.

Example 5

(E)-4-(4-(3-(3-hydroxyphenyl)acrylamido)phenoxy)-N-methylpicolinamide (6g)

To a solution of (E)-3-(3-hydroxyphenyl)acrylic acid (82 mg, 0.5 mmol) in dry dimethylformamide, EDCI (115 mg, 0.6 mmol) and HOBT (81 mg, 0.6 mmol) were added at 0° C. and the reaction mixture was stirred for 20 min. To the reaction mixture 4-(4-aminophenoxy)-N-methylpicolinamide (121.5 mg, 0.5 mmol) was added and stirred at room temperature (25° C.) for 12 h. The contents of the reaction mixture were poured into ice-cold water (25 mL), extracted with ethyl acetate (3×15.0) and the combined organic phase was washed with brine, dried over anhydrous sodium sulfate, filtered and concentrated in vacuo. The obtained residue was purified by column chromatography using ethyl acetate-hexane (0-50%) as eluent to give 136 mg (70%) of analytically pure compound (6g). mp: 180-182° C.; $^1$H NMR (CDCl3): δ 9.89 (s, 1H), 9.14 (s, 1H), 8.40 (d, J=5.66 Hz, 1H), 8.20 (d, J=4.91 Hz, 1H), 7.82 (d, J=8.87 Hz, 2H), 7.66-7.53 (m, 3H), 7.21 (t, J=7.93 Hz, 1H), 7.07-7.00 (s, 4H), 6.97 (dd, J=2.45, 5.66 Hz, 1H), 6.86 (dd, J=1.51, 7.93 Hz, 1H), 6.75 (d, J=15.48 Hz, 1H), 2.99 (d, J=5.09 Hz, 3H); MS (ESI): m/z 390 [M+H]$^+$.

Example 6

(E)-4-(4-(3-(4-chlorophenyl)acrylamido)phenoxy)-N-methylpicolinamide (6l)

To a solution of (E)-3-(4-chlorophenyl)acrylic acid (91.3 mg, 0.5 mmol) in dry dimethylformamide, EDCI (115 mg, 0.6 mmol) and HOBT (81 mg, 0.6 mmol) were added at 0° C. and the reaction mixture was stirred for 20 min. To the reaction mixture 4-(4-aminophenoxy)-N-methylpicolinamide (121.5 mg, 0.5 mmol) was added and stirred at room temperature (25° C.) for 12 h. The contents of the reaction mixture were poured into ice-cold water (25 mL), extracted with ethyl acetate (3×15.0) and the combined organic phase was washed with brine, dried over anhydrous sodium sulfate, filtered and concentrated in vacuo. The obtained residue was purified by column chromatography using ethyl acetate-hexane (0-50%) as eluent to give 146 mg (72%) of analytically pure compound (6l). mp: 192-195° C.; $^1$H NMR (CDCl3): δ 8.39 (d, J=5.64 Hz, 1H), 8.15 (s, 1H), 8.07 (d, J=4.88 Hz, 1H), 7.72-7.67 (m, 3H), 7.65 (d, J=2.44 Hz, 1H), 7.42 (d, J=8.54 Hz, 2H), 7.34 (d, J=8.39 Hz, 2H), 7.04 (d, J=8.85 Hz, 2H), 6.99 (dd, J=2.44, 5.49 Hz, 1H), 6.56 (d, J=15.41 Hz, 1H), 3.02 (d, J=5.18 Hz, 3H); MS (ESI): m/z 408 [M+H]$^+$.

Example 7

(E)-4-(4-(3-(4-fluorophenyl)acrylamido)phenoxy)-N-methylpicolinamide (6o)

To a solution of (E)-3-(4-fluorophenyl)acrylic acid (83 mg, 0.5 mmol) in dry dimethylformamide, EDCI (115 mg, 0.6 mmol) and HOBT (81 mg, 0.6 mmol) were added at 0° C. and the reaction mixture was stirred for 20 min. To the reaction mixture 4-(4-aminophenoxy)-N-methylpicolinamide (121.5 mg, 0.5 mmol) was added and stirred at room temperature (25° C.) for 12 h. The contents of the reaction mixture were poured into ice-cold water (25 mL), extracted with ethyl acetate (3×15.0) and the combined organic phase was washed with brine, dried over anhydrous sodium sulfate, filtered and concentrated in vacuo. The obtained residue was purified by column chromatography using ethyl acetate-hexane (0-50%) as eluent to give 150 mg (77%) of analytically pure compound (6o). mp: 222-224° C.; $^1$H NMR (CDCl3+DMSO): δ 9.79 (s, 1H), 8.39 (d, J=5.47 Hz, 1H), 8.15 (d, J=4.15 Hz, 1H), 7.81 (d, J=8.87 Hz, 2H), 7.71-7.64 (m, 2H), 7.56 (q, J=5.47, 8.49 Hz, 2H), 7.13-7.03 (m, 4H), 6.97 (dd, J=2.45, 5.66 Hz, 1H), 6.72 (d, J=15.67 Hz, 1H), 3.00 (d, J=5.09 Hz, 3H); MS (ESI): m/z 392 [M+H]$^+$.

Example 8

(E)-4-(4-(3-(3,4-difluorophenyl)acrylamido)phenoxy)-N-methylpicolinamide (6q)

To a solution of (E)-3-(3,4-difluorophenyl)acrylic acid (92 mg, 0.5 mmol) in dry dimethylformamide, EDCI (115 mg, 0.6 mmol) and HOBT (81 mg, 0.6 mmol) were added at 0° C. and the reaction mixture was stirred for 20 min. To the reaction mixture 4-(4-aminophenoxy)-N-methylpicolinamide (121.5 mg, 0.5 mmol) was added and stirred at room temperature (25° C.) for 12 h. The contents of the reaction mixture were poured into ice-cold water (25 mL), extracted with ethyl acetate (3×15.0) and the combined organic phase was washed with brine, dried over anhydrous sodium sulfate, filtered and concentrated in vacuo. The obtained residue was purified by column chromatography using ethyl acetate-hexane (0-50%) as eluent to give 155 mg (76%) of analytically pure compound (6q). mp: 208-210° C.; $^1$H NMR (CDCl3): δ 8.40 (d, J=5.62 Hz, 2H), 8.10 (d, J=4.76 Hz, 1H), 7.70 (d, J=8.55 Hz, 2H), 7.64 (d, J=15.89 Hz, 2H), 7.06-7.00 (m, 3H), 6.96 (d, J=6.11 Hz, 2H), 6.84-6.78 (m, 1H), 6.58 (d, J=15.52 Hz, 1H), 3.03 (d, J=5.13 Hz, 3H); MS (ESI): m/z 410 [M+H]$^+$.

Example 9

(E)-N-methyl-4-(4-(3-(4-(trifluoromethyl)phenyl)acrylamido)phenoxy)picolinamide (6t)

To a solution of (E)-3-(4-(trifluoromethyl)phenyl)acrylic acid (94.5 mg, 0.5 mmol) in dry dimethylformamide, EDCI (115 mg, 0.6 mmol) and HOBT (81 mg, 0.6 mmol) were added at 0° C. and the reaction mixture was stirred for 20 min. To the reaction mixture 4-(4-aminophenoxy)-N-methylpicolinamide (121.5 mg, 0.5 mmol) was added and stirred at room temperature (25° C.) for 12 h. The contents of the reaction mixture were poured into ice-cold water (25 mL), extracted with ethyl acetate (3×15.0) and the combined organic phase was washed with brine, dried over anhydrous sodium sulfate, filtered and concentrated in vacuo. The obtained residue was purified by column chromatography using ethyl acetate-hexane (0-50%) as eluent to give 163 mg (74%) of analytically pure compound (6t). mp: 210-212° C.; $^1$H NMR (CDCl3+DMSO): δ 10.06 (s, 1H), 8.40 (d, J=5.47 Hz, 1H), 8.23 (d, J=4.72 Hz, 1H), 7.83 (d, J=8.87 Hz, 2H), 7.73 (d, J=9.25 Hz, 1H), 7.70-7.63 (m, 5H), 7.08 (d, J=8.87 Hz, 2H), 6.98 (dd, J=2.45, 5.47 Hz, 1H), 6.92 (d, J=15.67 Hz, 1H), 2.99 (d, J=5.09 Hz, 3H); MS (ESI): m/z 442 [M+H]$^+$.

Example 10

(E)-N-methyl-4-(4-(3-(4-(trifluoromethoxy)phenyl)acrylamido)phenoxy)picolinamide (6w)

To a solution of (E)-3-(4-(trifluoromethoxy)phenyl)acrylic acid (116 mg, 0.5 mmol) in dry dimethylformamide, EDCI (115 mg, 0.6 mmol) and HOBT (81 mg, 0.6 mmol) were added at 0° C. and the reaction mixture was stirred for 20 min. To the reaction mixture 4-(4-aminophenoxy)-N-methylpicolinamide (121.5 mg, 0.5 mmol) was added and stirred at room temperature (25° C.) for 12 h. The contents of the reaction mixture were poured into ice-cold water (25 mL), extracted with ethyl acetate (3×15.0) and the combined organic phase was washed with brine, dried over anhydrous sodium sulfate, filtered and concentrated in vacuo. The obtained residue was purified by column chromatography using ethyl acetate-hexane (0-50%) as eluent to give 173 mg (76%) of analytically pure compound (6w). mp: 198-200° C.; $^1$H NMR (CDCl3+DMSO): δ 10.01 (s, 1H), 8.39 (d, J=4.34 Hz, 1H), 8.20 (s, 1H), 7.83 (d, J=7.74 Hz, 2H), 7.56-7.40 (m, 4H), 7.23 (d, J=4.53 Hz, 1H), 7.07 (d, J=7.93 Hz, 2H), 6.97 (s, 1H), 6.86 (d, J=15.67 Hz, 1H), 3.01 (d, J=6.04 Hz, 3H); MS (ESI): m/z 458 [M+H]$^+$.

Example 11

(E)-4-(4-(3-(furan-2-yl)acrylamido)phenoxy)-N-methylpicolinamide (7b)

To a solution of (E)-3-(furan-2-yl)acrylic acid (69 mg, 0.5 mmol) in dry dimethylformamide, EDCI (115 mg, 0.6 mmol) and HOBT (81 mg, 0.6 mmol) were added at 0° C. and the reaction mixture was stirred for 20 min. To the reaction mixture 4-(4-aminophenoxy)-N-methylpicolinamide (121.5 mg, 0.5 mmol) was added and stirred at room temperature (25° C.) for 12 h. The contents of the reaction mixture were poured into ice-cold water (25 mL), extracted with ethyl acetate (3×15.0) and the combined organic phase was washed with brine, dried over anhydrous sodium sulfate, filtered and concentrated in vacuo. The obtained residue was purified by column chromatography using ethyl acetate-hexane (0-50%) as eluent to give 127 mg (70%) of analytically pure compound (7b). mp: 163-165° C.; $^1$H NMR (CDCl3): δ 8.38 (d, J=5.64 Hz, 1H), 8.04 (d, J=4.42 Hz, 1H), 7.88 (s, 1H), 7.69 (d, J=2.28 Hz, 2H), 7.67 (s, 1H), 7.53 (d, J=15.10 Hz, 1H), 7.45 (s, 1H), 7.04 (d, J=8.85 Hz, 2H), 6.96 (q, J=2.59, 5.64 Hz, 1H), 6.60 (d, J=3.35 Hz, 1H), 6.49 (d, J=14.95 Hz, 1H), 6.47 (d, J=1.83 Hz, 1H), 3.02 (d, J=5.18 Hz, 3H); MS (ESI): m/z 364 [M+H]$^+$.

Example 12

(E)-N-methyl-4-(4-(3-(thiophen-2-yl)acrylamido)phenoxy)picolinamide (7g)

To a solution of (E)-3-(thiophen-2-yl)acrylic acid (77 mg, 0.5 mmol) in dry dimethylformamide, EDCI (115 mg, 0.6 mmol) and HOBT (81 mg, 0.6 mmol) were added at 0° C. and the reaction mixture was stirred for 20 min. To the reaction mixture 4-(4-aminophenoxy)-N-methylpicolinamide (121.5 mg, 0.5 mmol) was added and stirred at room temperature (25° C.) for 12 h. The contents of the reaction mixture were poured into ice-cold water (25 mL), extracted with ethyl acetate (3×15.0) and the combined organic phase was washed with brine, dried over anhydrous sodium sulfate, filtered and concentrated in vacuo. The obtained residue was purified by column chromatography using ethyl acetate-hexane (0-50%) as eluent to give 140 mg (74%) of analytically pure compound (7g). mp: 183-185° C.; $^1$H NMR (CDCl3): δ 8.38 (d, J=5.49 Hz, 1H), 8.05 (d, J=4.73 Hz, 1H), 7.90 (s, 1H), 7.87 (d, J=15.25 Hz, 1H), 7.68 (q, J=3.20, 5.79 Hz, 3H), 7.34 (d, J=5.03 Hz, 1H), 7.25 (d, J=3.35 Hz, 1H), 7.07-7.03 (m, 3H), 6.97 (dd, J=2.59, 5.49 Hz, 1H), 6.38 (d, J=15.10 Hz, 1H), 3.02 (d, J=5.18 Hz, 3H); MS (ESI): m/z 380 [M+H]$^+$.

Biological Activity

The cytotoxic activity studies for these (E)-4-(4-acrylamidophenoxy)-N-methylpicolinamide conjugates were carried out at the Medicinal Chemistry and Pharmacology, CSIR-Indian Institute of Chemical Technology, Hyderabad, India.

Cytotoxic Activity

The (E)-4-(4-acrylamidophenoxy)-N-methylpicolinamide conjugates of general formulae 6a-6z and 7a-7aj have been evaluated for their cytotoxicity in selected human cancer cell lines i.e., lung (A549), prostate (DU-145), ovarian (SKOV3) and liver (HepG2) using MTT assay and the values obtained were compared to a standard drug sorafenib, with the concentration (treatment done at ranging from 10$^{-4}$ to 10$^{-8}$ M) of the compound produces to 50% inhibition of cell growth (IC$_{50}$) as shown in Table 1. The screening results suggested that the selected compounds 6b, 6c, 6d, 6e, 6g, 6l, 6m, 6o, 6p, 6q, 6t, 6z, 7b and 7g exhibit significant cytotoxicity against a different set of human cancer cell lines. The IC$_{50}$ values (in μM) for compounds 6b, 6c, 6d, 6e, 6g, 6l, 6m, 6o, 6p, 6q, 6t, 6z, 7b and 7g have been illustrated in Table 1.

From the Table 1, it is seen that compounds 6b, 6c, 6d, 6e, 6g, 6l, 6m, 6o, 6p, 6q, 6t, 6z, 7b and 7g exhibit significant activity more specifically against HepG2 (liver cancer) among the four different types of cancer cell lines examined, with IC$_{50}$ values ranging from 8 to 13 μM. Predominantly, these compounds show superior cytotoxicity than the standard drug sorafenib i.e. 14.5 μM on HepG2 (liver cancer) cell line. Moreover, compound 6t exhibits remarkable cytotoxicity (8.2 μM) compared to other compounds has revealed in the Table 1. In the same way, the compounds 6b, 6l, 6d, 6e and 7b were more potent than the other compounds like 6c, 6g, 6m, 6o, 6p, 6q, 6z and 7g. The IC$_{50}$ values (in μM) for the compounds 6b, 6d, 6e, 6l and 7b against HepG2 (liver cancer) cell line were 9.5, 10.2, 10.1, 9.6 and 10.2 μM respectively.

TABLE 1

IC$_{50}$ values (in μM) for compounds in selected human cancer cell lines

| Compound[a] | A549[b] | DU145[c] | SKOV3[d] | HepG2[e] |
|---|---|---|---|---|
| 6b | — | — | 10.6 ± 0.32 | 9.5 ± 0.08 |
| 6c | — | — | — | 12.4 ± 0.16 |
| 6d | — | 21.1 ± 0.18 | — | 10.2 ± 0.22 |
| 6e | — | 29.5 ± 0.26 | — | 10.1 ± 0.15 |
| 6g | — | — | 12.0 ± 0.11 | 10.9 ± 0.22 |
| 6l | — | 17.9 ± 0.24 | 12.6 ± 0.28 | 9.6 ± 0.16 |
| 6m | 9.5 ± 0.22 | 23.3 ± 0.28 | — | 12.4 ± 0.32 |
| 6o | — | — | — | 12.5 ± 0.18 |
| 6p | 49.4 ± 0.54 | — | — | 13.1 ± 0.26 |
| 6q | — | — | 11.2 ± 0.26 | 11.1 ± 0.14 |
| 6t | 22.3 ± 0.22 | — | — | 8.2 ± 0.09 |
| 6z | 30.1 ± 0.28 | 28.7 ± 0.36 | — | 12.2 ± 0.22 |
| 7b | — | — | — | 10.2 ± 0.11 |
| 7g | 24.1 ± 0.44 | 12.2 ± 0.26 | — | 13.2 ± 0.11 |
| Sorafenib | 6.1 ± 0.18 | 6.5 ± 0.22 | 9.5 ± 0.12 | 14.5 ± 0.16 |

[a]50% Inhibitory concentration after 48 h of drug treatment and the values are average of three individual experiments,
[b]Human lung cancer,
[c]Human prostate cancer,
[d]Human ovarian cancer,
[e]Liver cancer.

Advantages of the Invention

The present invention provides some new (E)-4-(4-acrylamidophenoxy)-N-methylpicolinamide conjugates useful as antitumor agents. In this present invention, the synthesized compounds have shown significant anticancer activity.

(E)-4-(4-Acrylamidophenoxy)-N-methylpicolinamide conjugates that have been synthesized exhibited potent cytotoxic activity against different human tumor cell lines.

It also provides a process for the preparation of new (E)-4-(4-acrylamidophenoxy)-N-methylpicolinamide conjugates.

We claim:

1. A compound of formula A:

Formula A

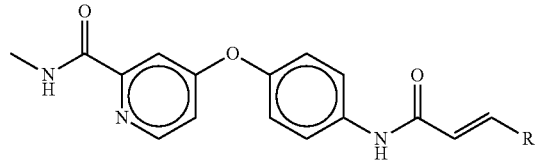

wherein R is selected from

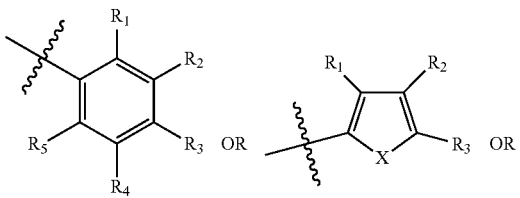

OR

-continued

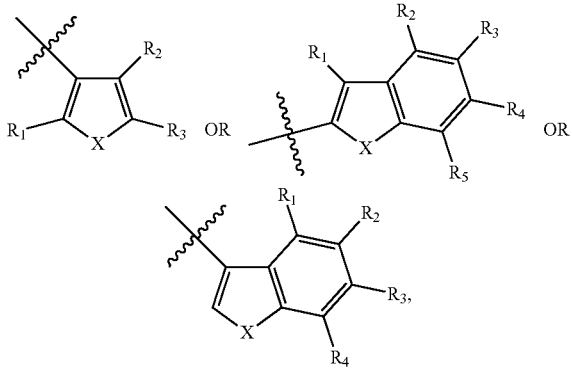

where $R_1$ to $R_5$ are independently selected from the group consisting of H, Cl, F, Br, $CH_3$, $C_2H_5$, $CH(CH_3)_2$, $OCH_3$, $CF_3$, $OCF_3$, OH, $NO_2$, and CN; and
X is selected from O, NH, or S.

2. The compound according to claim 1, wherein the compound is selected from the group consisting of:
- (E)-4-(4-(3-(2-methoxyphenyl)acrylamido)phenoxy)-N-methylpicolinamide (6a);
- (E)-4-(4-(3-(4-methoxyphenyl)acrylamido)phenoxy)-N-methylpicolinamide (6b);
- (E)-4-(4-(3-(2,3-dimethoxyphenyl)acrylamido)phenoxy)-N-methylpicolinamide (6c);
- (E)-N-methyl-4-(4-(3-(3,4,5-trimethoxyphenyl)acrylamido)phenoxy)picolinamide (6d);
- (E)-4-(4-(3-(2,5-dimethoxyphenyl)acrylamido)phenoxy)-N-methylpicolinamide (6e);
- (E)-4-(4-(3-(3,4-dimethoxyphenyl)acrylamido)phenoxy)-N-methylpicolinamide (6f);
- (E)-4-(4-(3-(3-hydroxyphenyl)acrylamido)phenoxy)-N-methylpicolinamide (6g);
- (E)-4-(4-(3-(4-hydroxyphenyl)acrylamido)phenoxy)-N-methylpicolinamide (6h);
- (E)-4-(4-(3-(3-hydroxy-4-methoxyphenyl)acrylamido)phenoxy)-N-methylpicolinamide (6i);
- (E)-4-(4-(3-(2-chlorophenyl)acrylamido)phenoxy)-N-methylpicolinamide (6j);
- (E)-4-(4-(3-(3-chlorophenyl)acrylamido)phenoxy)-N-methylpicolinamide (6k);
- (E)-4-(4-(3-(4-chlorophenyl)acrylamido)phenoxy)-N-methylpicolinamide (6l);
- (E)-4-(4-(3-(3,4-dichlorophenyl)acrylamido)phenoxy)-N-methylpicolinamide (6m);
- (E)-4-(4-(3-(3-fluorophenyl)acrylamido)phenoxy)-N-methylpicolinamide (6n);
- (E)-4-(4-(3-(4-fluorophenyl)acrylamido)phenoxy)-N-methylpicolinamide (6o);
- (E)-4-(4-(3-(2,4-difluorophenyl)acrylamido)phenoxy)-N-methylpicolinamide (6p);
- (E)-4-(4-(3-(3,4-difluorophenyl)acrylamido)phenoxy)-N-methylpicolinamide (6q);
- (E)-N-methyl-4-(4-(3-(2-(trifluoromethyl)phenyl)acrylamido)phenoxy)picolinamide (6r);
- (E)-N-methyl-4-(4-(3-(3-(trifluoromethyl)phenyl)acrylamido)phenoxy)picolinamide (6s);
- (E)-N-methyl-4-(4-(3-(4-(trifluoromethyl)phenyl)acrylamido)phenoxy)picolinamide (6t);
- (E)-N-methyl-4-(4-(3-(2-(trifluoromethoxy)phenyl)acrylamido)phenoxy)picolinamide (6u);
- (E)-N-methyl-4-(4-(3-(3-(trifluoromethoxy)phenyl)acrylamido)phenoxy)picolinamide (6v);
- (E)-N-methyl-4-(4-(3-(4-(trifluoromethoxy)phenyl)acrylamido)phenoxy)picolinamide (6w);
- (E)-4-(4-(3-(4-fluoro-3-(trifluoromethoxy)phenyl)acrylamido)phenoxy)-N-methylpicolinamide (6x);
- (E)-4-(4-(3-(4-chloro-3-(trifluoromethoxy)phenyl)acrylamido)phenoxy)-N-methylpicolinamide (6y);
- (E)-N-methyl-4-(4-(3-(4-nitrophenyl)acrylamido)phenoxy)picolinamide (6z);
- (E)-4-(4-(3-(1H-pyrrol-3-yl)acrylamido)phenoxy)-N-methylpicolinamide (7a);
- (E)-4-(4-(3-(furan-2-yl)acrylamido)phenoxy)-N-methylpicolinamide (7b);
- (E)-N-methyl-4-(4-(3-(5-methylfuran-2yl)acrylamido)phenoxy)picolinamide (7c);
- (E)-4-(4-(3-(5-ethylfuran-2-yl)acrylamido)phenoxy)-N-methylpicolinamide (7d);
- (E)-4-(4-(3-(3-bromofuran-2-yl)acrylamido)phenoxy)-N-methylpicolinamide (7e);
- (E)-N-methyl-4-(4-(3-(5-nitrofuran-2-yl)acrylamido)phenoxy)picolinamide (7f);
- (E)-N-methyl-4-(4-(3-(thiophen-2-yl)acrylamido)phenoxy)picolinamide (7g);
- (E)-4-(4-(3-(4-bromothiophen-2-yl)acrylamido)phenoxy)-N-methylpicolinamide (7h);
- (E)-N-methyl-4-(4-(3-(3-methylthiophen-2-yl)acrylamido)phenoxy)picolinamide (7i);
- (E)-4-(4-(3-(5-cyanothiophen-2-yl)acrylamido)phenoxy)-N-methylpicolinamide (7j);
- (E)-N-methyl-4-(4-(3-(4-methylthiophen-2-yl)acrylamido)phenoxy)picolinamide (7k);
- (E)-N-methyl-4-(4-(3-(5-methylthiophen-2-yl)acrylamido)phenoxy)picolinamide (7l);
- (E)-4-(4-(3-(benzofuran-2-yl)acrylamido)phenoxy)-N-methylpicolinamide (7m);
- (E)-4-(4-(3-(7-methoxybenzofuran-2-yl)acrylamido)phenoxy)-N-methylpicolinamide (7n);
- (E)-4-(4-(3-(benzo[b]thiophen-2-yl)acrylamido)phenoxy)-N-methylpicolinamide (7o);
- (E)-4-(4-(3-(3-bromobenzo[b]thiophen-2-yl)acrylamido)phenoxy)-N-methylpicolinamide ('7p);
- (E)-N-methyl-4-(4-(3-(3-methylbenzo[b]thiophen-2-yl)acrylamido)phenoxy)picolinamide (7q);
- (E)-4-(4-(3-(3-chlorobenzo[b]thiophen-2-yl)acrylamido)phenoxy)-N-methylpicolinamide (7r);
- (E)-N-methyl-4-(4-(3-(5-methylbenzo[b]thiophen-2-yl)acrylamido)phenoxy)picolinamide (7s);
- (E)-N-methyl-4-(4-(3-(4-methylbenzo[b]thiophen-2-yl)acrylamido)phenoxy)picolinamide (7t);
- (E)-4-(4-(3-(1H-indol-3-yl)acrylamido)phenoxy)-N-methylpicolinamide (7u);
- (E)-N-methyl-4-(4-(3-(7-methyl-1H-indol-3-yl)acrylamido)phenoxy)picolinamide (7v);
- (E)-4-(4-(3-(7-ethyl-1H-indol-3-yl)acrylamido)phenoxy)-N-methylpicolinamide (7w);
- (E)-4-(4-(3-(6-isopropyl-1H-indol-3-yl)acrylamido)phenoxy)-N-methylpicolinamide (7x);
- (E)-4-(4-(3-(5-chloro-1H-indol-3-yl)acrylamido)phenoxy)-N-methylpicolinamide ('7y);
- (E)-4-(4-(3-(6-chloro-1H-indol-3-yl)acrylamido)phenoxy)-N-methylpicolinamide (7z);
- (E)-4-(4-(3-(5-fluoro-1H-indol-3-yl)acrylamido)phenoxy)-N-methylpicolinamide (7aa);
- (E)-4-(4-(3-(6-fluoro-1H-indol-3-yl)acrylamido)phenoxy)-N-methylpicolinamide (7ab);
- (E)-4-(4-(3-(5-bromo-1H-indol-3-yl)acrylamido)phenoxy)-N-methylpicolinamide (7ac);

(E)-4-(4-(3-(6-bromo-1H-indol-3-yl)acrylamido)phenoxy)-N-methylpicolinamide (7ad);

(E)-4-(4-(3-(5-cyano-1H-indol-3-yl)acrylamido)phenoxy)-N-methylpicolinamide (7ae);

(E)-4-(4-(3-(6-cyano-1H-indol-3-yl)acrylamido)phenoxy)-N-methylpicolinamide (7af);

(E)-N-methyl-4-(4-(3-(5-methyl-1H-indol-3-yl)acrylamido)phenoxy)picolinamide (7ag);

(E)-N-methyl-4-(4-(3-(6-methyl-1H-indol-3-yl)acrylamido)phenoxy)picolinamide (7ah);

(E)-N-methyl-4-(4-(3-(5-nitro-1H-indol-3-yl)acrylamido)phenoxy)picolinamide (7a1); and (E)-N-methyl-4-(4-(3-(6-nitro-1H-indol-3-yl)acrylamido)phenoxy)picolinamide (7aj).

3. The compound according to claim 1, wherein said compound exhibits cytotoxic activity against cancer cell lines selected from the group consisting of non-small cell lung cancer, colon cancer, prostate cancer, ovarian cancer, and liver cancer.

4. The compound according to claim 1, wherein an $IC_{50}$ value for 50% inhibition of cell growth of cancer cells of the compound of formula A, using in-vitro MTT assay is in the range of 8 μM to 13 μM.

5. A process for the preparation of compounds of formula A, the process comprising:

(i) mixing acid compound of formula 4 with 1-Ethyl-3-(3-dimethylaminopropyl)carbodiimide and Hydroxybenzotriazole, under stirring at a temperature in the range of 0 to 10° C. for 15 to 20 minutes in a solvent to obtain a mixture;

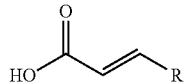

wherein R is selected from

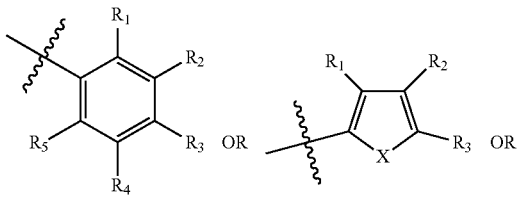

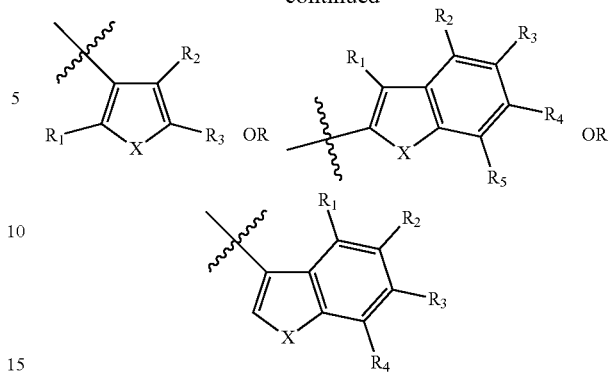

where $R_1$ to $R_5$ is independently are independently selected from the group consisting of H, Cl, F, Br, $CH_3$, $C_2H_5$, $CH(CH_3)_2$, $OCH_3$, $CF_3$, $OCF_3$, OH, $NO_2$ and CN; and X is selected from O, NH, or S;

(ii) adding 4-(4-aminophenoxy)-N-methylpicolinamide of formula 3 in the mixture as obtained in (i) with stirring at a temperature in the range of 20 to 30° C. for 10 to 12 hours to obtain a mixture; and

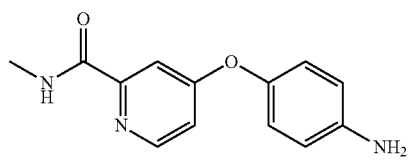

(iii) cooling the mixture as obtained in (ii), extracting, washing, drying, filtering and purifying by column chromatography to obtain the compound of formula A:

Formula A

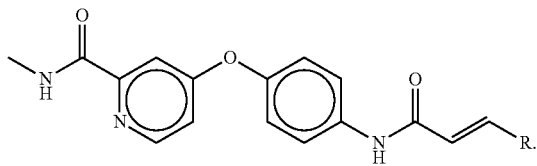

6. The process according to claim 5, wherein the solvent is dimethylformamide (DMF) and DCM.

* * * * *